(12) United States Patent
Denney (10) Patent No.: US 9,964,557 B2
(45) Date of Patent: May 8, 2018

(54) APPARATUS FOR OPTICAL MICROFLUIDICS SLUG EDGE DETECTION

(71) Applicant: Canon U.S. Life Sciences, Inc., Rockville, MD (US)

(72) Inventor: Bradley Scott Denney, Irvine, CA (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 0 days. days.

(21) Appl. No.: 14/597,595

(22) Filed: Jan. 15, 2015

(65) Prior Publication Data

US 2015/0211049 A1 Jul. 30, 2015

Related U.S. Application Data

(60) Provisional application No. 61/927,884, filed on Jan. 15, 2014.

(51) Int. Cl.

| | |
|---|---|
| *G06T 7/143* | (2017.01) |
| *G01N 35/08* | (2006.01) |
| *G06T 7/13* | (2017.01) |
| *G06T 7/12* | (2017.01) |
| *G06T 7/194* | (2017.01) |
| *B01L 3/00* | (2006.01) |

(52) U.S. Cl.
CPC .............. *G01N 35/08* (2013.01); *G06T 7/12* (2017.01); *G06T 7/13* (2017.01); *G06T 7/143* (2017.01); *B01L 3/502784* (2013.01); *G06T 2207/10024* (2013.01); *G06T 2207/30108* (2013.01)

(58) Field of Classification Search
None
See application file for complete search history.

(56) References Cited

U.S. PATENT DOCUMENTS

| | | | |
|---|---|---|---|
| 7,314,070 B2 | 1/2008 | Jeon et al. | |
| 8,263,392 B2 | 9/2012 | Gale et al. | |
| 2004/0180346 A1* | 9/2004 | Anderson | ............ C12Q 1/6806 435/6.18 |

(Continued)

OTHER PUBLICATIONS

Matas et al., "Spatial and Feature Space Clustering: Applications in Image Analysis," 6th Int. Conf. on Computer Analysis and Patterns , Prague, Czech Republic, Sep. 1995.

(Continued)

*Primary Examiner* — Neil N Turk
(74) *Attorney, Agent, or Firm* — Canon U.S.A., Inc., IP Dept.

(57) ABSTRACT

A system and a method for slug edge detection in a microchannel of a microfluidic device is provided. Specifically, the system comprises an image sensor in communication with the microchannel. The microchannel has at least two fluid slugs each of which has a marker of different color providing color gradient across the edge between the adjacent fluid slugs. An edge score function is generated for each channel segmentation dividing the microchannel into two segments at a specific location along the microchannel. The edge score function is proportional to a between class variance for intensity values associated with the two selected channel segments. The edge location is determined as the location along the channel defining one of the channel segmentations based at least in part on the edge score function.

35 Claims, 7 Drawing Sheets

(56) References Cited

U.S. PATENT DOCUMENTS

| | | | |
|---|---|---|---|
| 2004/0189311 A1* | 9/2004 | Glezer | B01L 3/5027 324/444 |
| 2007/0039866 A1* | 2/2007 | Schroeder | C12Q 1/6806 210/265 |
| 2008/0003588 A1* | 1/2008 | Hasson | G06T 7/11 435/6.11 |
| 2010/0044232 A1 | 2/2010 | Lin et al. | |
| 2012/0052560 A1 | 3/2012 | Knight et al. | |
| 2012/0058460 A1 | 3/2012 | Coursey et al. | |
| 2013/0177913 A1 | 7/2013 | Hasson et al. | |
| 2014/0272927 A1 | 9/2014 | Coursey et al. | |

OTHER PUBLICATIONS

Pietrzkiewicz, "Image Analysis Techniques for IndustrialInspection Systems," Master Thesis, Oct. 3, 2012.

Han et a., "Optimal Segmentation of Signals and Its Application to Image Denoising and Boundary Feature Extraction," preprint.

Schneider et al., "Optimal Segmentation of Signals and Its Application to Image Denoising and Boundary Feature Extraction," report, Jan. 1997.

Zong, "Image Segmentation for Defect Detection on Veneer Surfaces," Doctoral Thesis, Nov. 1, 1994.

Sezgin et al., "Survey over image thresholding techniques and quantitative performance evaluation". Journal of Electronic Imaging 13 (1), 2004: 146-165. doi:10.1117/1.1631315.

Otsu, "A threshold selection method from gray-level histograms". IEEE Trans. Sys., Man., Cyber. 9 (1), 1979: 62-66. doi:10.1109/TSMC.1979.4310076.

Liao et al., "A Fast Algorithm for Multilevel Thresholding". J. Inf. Sci. Eng. 17 (5), 2001: 713-727.

\* cited by examiner

APPARATUS FOR OPTICAL MICROFLUIDICS SLUG EDGE DETECTION

CROSS-REFERENCE TO RELATED APPLICATIONS

This application claims the benefit of U.S. Provisional Patent Application Ser. No. 61/927,884, filed on Jan. 15, 2014, which is incorporated herein by reference in its entirety.

BACKGROUND

1. Field of the Invention

The present invention relates to a method and system for controlling fluid flow in one or more channels of a microfluidic device used for performing biological reactions. Specifically, the present invention relates to detecting the edge between fluid slugs having markers of different colors in a channel of the microfluidic device and controlling the flow of the fluid slugs based on the edge location.

2. Discussion of the Background

Microfluidic devices are widely known and used for performing biological reactions. A number of approaches have been developed to control fluid flow in a microfluidic device. Specifically, flow control in microfluidic devices including multiple channels has been described in US Patent Application Publications No. 2014/0272927, No. 2013/0177913, No. 2012/0058460, No. 2012/0052560 the disclosures of which are hereby incorporated by reference. Many microfluidic devices known in the art include microchannels having sequentially alternating test solutions and carrier fluid. The purpose of the carrier fluid, ("blanking slugs") is to deter transfer of material from one test solution to another. Another purpose of the carrier fluid is to provide a distinguishable transition between slugs that may be used to track and control the fluid flow in the microchannel. The carrier fluid and the test solution may include fluorescent markers to allow for detecting the edge between adjacent slugs to track and control the fluid flow in the microchannel. A detector is usually provided to detect the progress of a biological reaction and track the fluid flow in the microchannel. Specifically, the detector can independently detect signals from one or more detectable markers. Biological reactions performed in the microfluidic devices may include a polymerase chain reaction (PCR) or a nucleic acid melting analysis. Other details of fluorescence imaging systems that may be used in connection with the microfluidic systems are described in U.S. Patent Application Publication No. 2008/0003594 the disclosure of which is hereby incorporated by reference.

Methods for controlling fluid flow in a microchannel of a microfluidic device based on the position of the edge between adjacent slugs have been developed and used. For instance, Coursey et al. (US Patent Application Publication No. 2012/0058460), the disclosure of which is hereby incorporated by reference, relate to a method of color thresholding using two color planes (e.g., blue and red) to obtain two measures of slug position: one based on the position of sample slugs (e.g., blue slugs) and one based on the position of blanking slugs (e.g., the red slugs). To identify an edge between two slugs, pixels that satisfy threshold conditions in a first wavelength plane of the image and a second wavelength plane of the image are identified. The threshold is usually pre-selected by the user.

Alternatively, Coursey et al. disclose using correlation methods, such as, for example, calculating a cross-correlation and covariance with a pre-determined template image, rather than threshold detection. Identifying an edge between the first slug and the second slug comprises cross-correlating the region of interest with a predetermined template image. A simple binary template image (black on one side and white on the other) is used to detect an edge of a slug. The transition from the black side to the white side of the pre-determined template image represents the slug edge. The black/white pre-defined template image is then cross-correlated with the slug images to determine the location of the slug edge (i.e., the position at which the correlation between the template and the image data is at a maximum or minimum).

Another approach to identifying location of the edge between adjacent fluid slugs in a microchannel is based on intensity gradient across the edge and employs Otsu's method ("A threshold selection method from gray-level histograms," IEEE Trans. Sys., Man., Cyber. 9 (1): 62-66 (1979)). Otsu's method is used to automatically perform clustering-based image thresholding. The method assumes that the image contains two classes of pixels (pixels of the first slug and pixels of the second slug) characterized by their intensities. The goal is to find an optimum intensity threshold defining the edge between the two slugs. Accordingly, Otsu's method employs image thresholding performed in intensity domain. In other words, the pixels of the image can be divided into two classes based on their intensities provided by an image histogram. The horizontal axis of the image histogram represents the intensity variations, while the vertical axis represents the number of pixels having that particular intensity. The optimum intensity threshold separating the two classes is calculated such that the intra-class variance is minimal (between-class variance is maximum). The calculated optimum intensity threshold combined with channel geometry defines the position of the edge between adjacent slugs in a channel.

Accordingly, to determine location of the edge between adjacent fluid slugs in a microchannel based on intensity gradient across the edge, the image histogram of a channel image is thresholded in the intensity domain to detect blob regions in the image. The blob regions presumably correspond to different slugs of interest. The microchannel is presumed to have a known location and orientation. The edge of the detected blobs is assumed to be the edge of interest. The detected blobs are validated against the presumed location of the channels. This approach generally works well in low noise scenarios, but its robustness can be compromised if there are bubbles or other imaging artifacts that cause broken or poorly defined blobs. Additionally, the technique may require some image pre-filtering to obtain good results, and the technique is relatively computationally expensive.

Accordingly, there is a need for a robust and simple solution that allows for detecting location of the edge between adjacent fluid slugs in a microchannel.

SUMMARY OF THE INVENTION

The present invention relates to detecting the edge between adjacent fluid slugs in a channel based upon color gradient across the edge. A flow control unit employs the position of the detected edge to control the position of the slugs in the channel.

In one aspect of the invention, a system and a method for detecting an edge between two adjacent fluid slugs in a channel are provided. Each slug includes a fluorescent marker of different color to provide a color gradient across the edge between the slugs. Furthermore, the system comprises an edge detection unit and an image sensor configured to acquire an image of at least a portion of the adjacent fluid slugs in the channel. The acquired image is characterized by an intensity signal changing at least along the channel. In one embodiment, the intensity signal characterizing the acquired image is a one-dimensional signal I(t) changing along the length the channel. In yet another embodiment, the intensity signal is a two-dimensional signal I(s, t) changing along and across the channel, wherein s is a coordinate changing across the channel and t is a coordinate changing along the channel.

In one embodiment, once the image of at least a portion of the adjacent fluid slugs is acquired, the edge detection unit provides instructions for a processing unit to convert intensify signal I(s, t) having one or more color components at each position defined by coordinates (s, t) to a monochrome intensity signal q(s, t) having only one component at each position defined by coordinates (s, t).

Furthermore, the edge detection unit is configured to provide instructions for the processing unit to convert the monochrome two-dimensional intensity signal q(s, t) changing along and across the channel into a one-dimensional intensity signal q(t) changing only along the length of the channel. Specifically, in one non-limiting embodiment, the two-dimensional intensity signal q(s, t) associated with the acquired image is converted into a one-dimensional intensity signal by integrating the image intensity signal q(s, t) in a cross channel direction from 0 to W, where W is the width of the channel.

Next, at least two different segmentations are sequentially applied to the length of the channel, wherein each of these segmentations partitions the length of the channel into two segments at a specific location $t_s$. In one embodiment, the segmentations are sequentially applied to the length of the channel such that $t_s$ is uniformly increasing from the first segmentation to the last segmentation.

In yet another non-limiting embodiment of the invention, the number of sequential segmentations applied to the length of the channel equals the number of pixels along the length of the channel. The number of segments in each of these segmentations equals to the number of slugs in the channel.

In the next step, the edge detection unit provides instructions to calculate an edge score function for each segmentation. The edge score function is proportional to a between class variance for intensity values associated with the two segments. A segmentation defining the edge location is selected based at least in part on the edge score function. In one embodiment, the edge location is defined by a segmentation maximizing the edge score function. Specifically, the location of the edge between two adjacent slugs is defined as a coordinate of the location selected to separate two segments of the channel and maximizing the edge score function.

In a non-limiting aspect of the invention, the between class variance is calculated as $$\sigma^2(t) = K \frac{\left[\frac{z(t)}{z(L)} - \frac{t}{L}\right]^2}{\frac{t}{L}\left(1 - \frac{t}{L}\right)} = Kv(t),$$

where v(t) is the edge score function, L is the length of the channel, W is the width of the channel, $z(t) = \int_0^t y(\tau)\, d\tau$, $y(t) = \int_0^W P\, I(s, t) ds = \int_0^W q(s, t) ds$, s is a coordinate orthogonal to t, I(s, t) is an intensity, P is a monochrome image producing transformation, and K is any finite positive number that is independent of t.

In yet another non-limiting aspect of the invention, left and right mean intensity signal values are calculated for the determined edge location and the edge direction is calculated based upon the determined left and right mean signal values. Specifically, the left and right mean intensity signals are calculated as $$\mu_{LEFT} = \frac{z(t^*)}{t^*} \text{ and } \mu_{RIGHT} = \frac{z(L) - z(t^*)}{L - t^*},$$

where t* defines the edge location between two adjacent slugs.

Accordingly, a segmentation maximizing the between class variance is selected by calculating the edge score for each segmentation and selecting a segmentation with the maximum edge score.

In yet another aspect of the invention, the system further comprises a flow control unit to control the flow of fluid slugs in the channel based on the determined edge location. In one non-limiting embodiment of the invention, the channel is a microchannel formed in a microfluidic device. The microchannel has at least one sample slug having a first fluorescent color marker and at least one blanking slug having a second fluorescent color marker. A biological reaction may be performed in the at least one sample slug. In one embodiment, a sample slug may be stopped in the microchannel while the biological reaction is performed. Alternatively, the sample slug may undergo continuous flow along the microchannel while the biological reaction is performed. In one non-limiting embodiment, at least one sample slug includes a nucleic acid of interest. A PCR amplification reaction and a nucleic acid melting analysis may be sequentially performed in at least one sample slug stopped or moving along the microchannel. In one embodiment, an image of the microchannel containing the edge between at least one sample slug and at least one blanking slug is acquired throughout the PCR reaction and melting analysis to control the sample slug position within the microchannel.

BRIEF DESCRIPTION OF THE DRAWINGS

The accompanying drawings, which are incorporated herein and form part of the specification, illustrate various embodiments of the subject matter of this disclosure. In the drawings, like reference numbers indicate identical or functionally similar elements.

DETAILED DESCRIPTION OF PREFERRED EMBODIMENTS

The present invention has several embodiments and relies on patents, patent applications, and other references for details known in the art. Therefore, when a patent, patent application, or other reference is cited or repeated herein, it should be understood that it is incorporated by reference in its entirety for all purposes as well as for the proposition that is recited.

One aspect of the present invention relates to a microfluidic system including one or more microchannels. In one non-limiting embodiment, the microfluidic system is a multi-slug system where each microchannel includes two or more sample slugs alternated by blanking slugs (carrier fluid). In yet another non-limiting embodiment of the invention, the microfluidic system is a single-slug system where no more than one sample slug at a time is present in each microchannel. As each blanking slug includes a first fluorescent color marker and each sample slug includes a second fluorescent color marker, fluorescence emitted from the blanking slugs has a different color than fluorescence emitted by the sample slugs. The color difference enables the blanking slugs to be spatially imaged and used for slug position sensing. Information about the sample and blanking slug position may be used to adjust the pressure applied to the downstream end of a microchannel and, thereby, control the positions of the sample and blanking slugs.

The multi-slug and single-slug systems may be operated in one of two flow modes: (1) stopped flow mode and (2) continuous flow mode. Specifically, in the stopped flow mode, a flow controller may hold one or more sample slugs in a fixed position or oscillate about a fixed position in a microchannel for the duration of a biological reaction. Alternatively, in the continuous flow mode, the flow controller may draw one or more slugs across the microchannel while the biological reaction is performed in one or more sample slugs. In one aspect of the invention, to control fluid flow in a microchannel of a microfluidic device, the edge between adjacent slugs is detected and flow control is provided by the controller based upon the location of the edge.

Alternatively, in some non-limiting embodiments, the present invention can be applied to a channel of any dimensions having adjacent fluid slugs demonstrating color gradient at the fluid transition. As a practical matter, the width of a slug is limited in order to limit the size of the channel cross-section thereby limiting the ability of the sample slug to mix with the blanking slug. A small cross-section guarantees a strong color gradient at the fluid transition.

Figure 1:
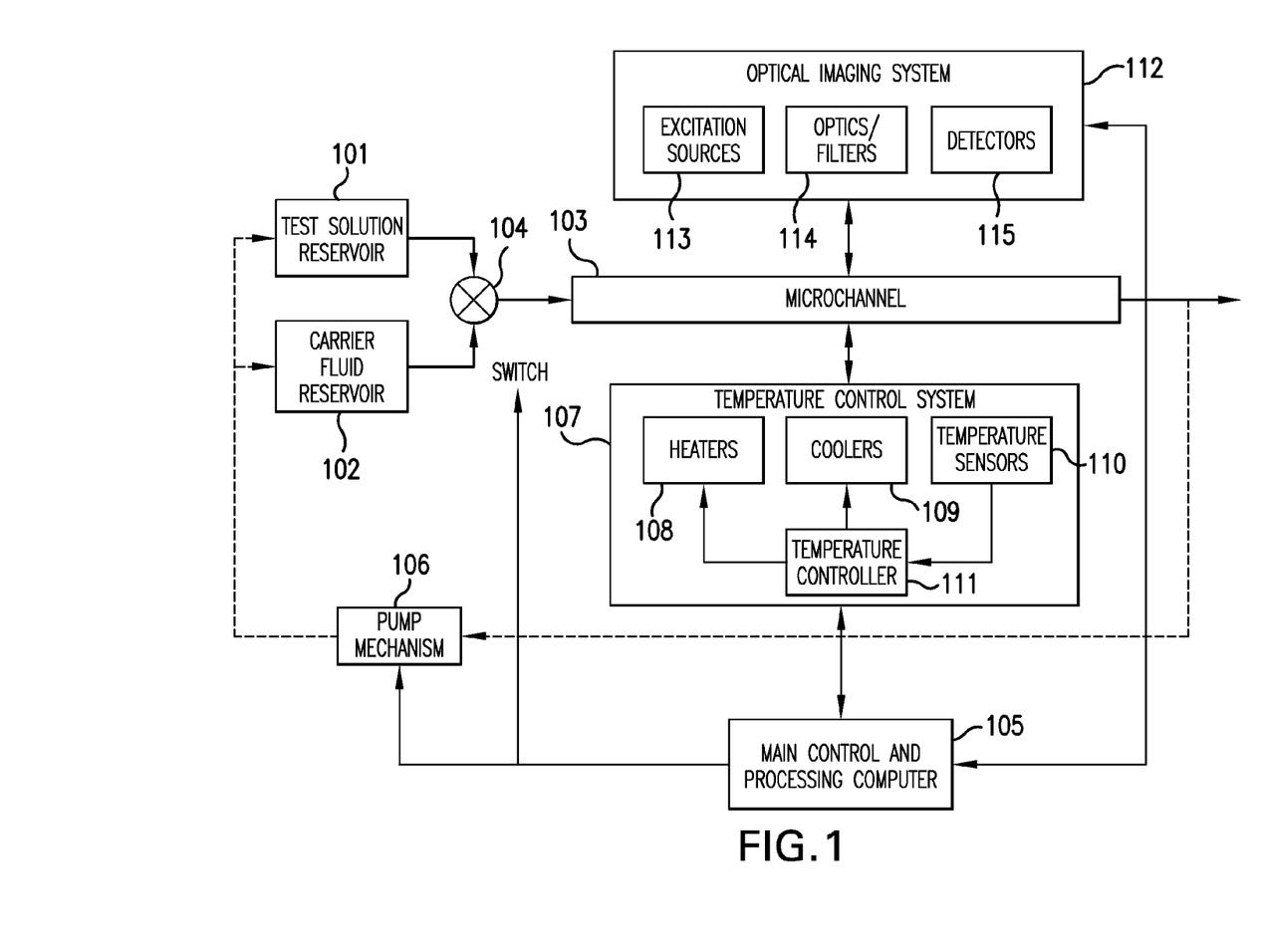
FIG. 1 is a block diagram illustrating a microfluidic system in accordance with one embodiment of the present invention.

FIG. 1 is a block diagram illustrating a microfluidic system in accordance with one embodiment of the present invention. The system includes a test/sample solution reservoir (101), which may be a reservoir containing multiple sample/test solutions. The system further includes a carrier fluid reservoir (102). In one embodiment, the test solution is substantially the same as the carrier fluid, except that the test solution comprises all necessary reagents for performing a biological reaction. Biological reactions that can be performed in the microfluidic device of FIG. 1 include but are not limited to PCR, real-time PCR, and melting analysis. As noted above, one of the purposes of the carrier fluid is to provide a distinguishable transition between slugs that may be used to track the fluid flow in the channel. In one embodiment, the carrier fluid and the sample solution may include a color marker.

The test solution and carrier fluid are introduced into a microchannel (103) through a switch (104). Microchannel (103) may be a single microchannel or it may be one of several microchannels that are part of a microfluidic device. Switch (104) is under control of a main control and processing computer (105) such that the carrier fluid and the test solution are sequentially alternately introduced into microchannel (103).

In one embodiment, microchannel (103) has two or more sample slugs separated by one or more blanking slugs. A multitude of reactions in series (or sequential reactions) can thus be carried out in the same microchannel (103) as a result of the continuous movement of different test solutions through microchannel (103). The flow rate of the carrier fluid and sample solution through microchannel (103) is controlled by pump mechanism (106). Pump mechanism (106) is under control of main control and processing computer (105) in order to regulate the flow of the sample solution and the carrier fluid in microchannel (103) by positive pressure at the upstream side or inlet of microchannel (103) or by negative pressure at the downstream side or outlet of microchannel (103).

In yet another embodiment, a single sample slug and a single blanking slug are present in microchannel (103). A biological reaction is performed in a stopped flow in the single sample slug. The sample slug and/or the blanking slug include different fluorescent color markers to detect the edge between the sample slug and the blanking slug. The position of the sample slug and the blanking slug within the channel is determined based upon the position of the observed edge between the sample slug and the blanking slug.

A temperature control system (107) is included in the system to control the temperature as the test solution moves through microchannel (103) while a biological reaction is performed. Temperature control system (107) is integral with or proximal to microchannel (103) or to the microchannels of a microfluidic device. Temperature control system (107) includes heaters (108), coolers (109), temperature sensors (110) and a temperature controller (111). Temperature controller (111) collects temperature information from the temperature sensors (110) and generates control signals based on the temperature information. In one embodiment, the control signals are sent to the heaters (108) or coolers (109) to cycle the temperature in microchannel (103) according to a PCR profile or to ramp the temperature according to a nucleic acid melting profile.

An optical imaging system (112) is included in the microfluidic system to monitor the fluid flow of the sample solution in microchannel (103). In one embodiment, the optical imaging system (112) is a fluorescent imaging system that preferably includes one or more excitation sources (113), one or more optics/filters (114) and one or more detectors (115). In one embodiment, excitation sources (113) generate light at desired wavelengths to detect fluorescent color markers that may be present to monitor the flow of the test solution in microchannel (103). Optics/filters (114) are used to form a beam of light and/or to direct the light from excitation sources (113) to the appropriate positions on microchannel (103). Detectors (115) may include multiple-pixel array detectors (such as a CCD detector) and/or discrete single-pixel. Detectors (115) may be integral with or proximal to microchannel (103) or to the microchannels of a microfluidic device. Detectors (115) may be stationary or may be scanning.

Optical imaging system (112) is under control of main control and processing computer (105) which directs the optical/fluorescence imaging system (112) to measure the intensity of the emitted light at desired time intervals, such as, for example, at least once during each PCR cycle at a plurality of locations in microchannel (103) or in the microchannels of a microfluidic device. Detectors (115) generate a signal or an image of the intensity of the emitted light and direct it to main control and processing computer (105) for analysis of the biological reaction and for controlling the fluid flow and position of sample and blanking slugs in one or more microchannels (103). In one embodiment, the flow control includes detecting the edge between adjacent slugs and determining the position of the edge along the length of microchannel (103).

In one embodiment, the PCR mixture may include a non-specific fluorescent DNA detecting molecule (such as an intercalating dye), a sequence-specific fluorescent DNA probe (such as a molecular beacon, a TaqMan® probe or a quantum dot probe), or a flow marker (such as a quantum dot), and the carrier fluid may include a flow marker. Optical imaging system (112) is utilized to detect the intensity of the fluorescence from the DNA detecting molecule or the probe (i.e., the intensity of the fluorescent signal) and/or to detect the fluorescence of the marker. The fluorescence of the marker can be used to delineate the test solution from the carrier fluid and to monitor the flow of the test solution and/or carrier fluid.

In a non-limiting embodiment, main control and processing computer (105) can be programmed to take the image at the time and temperature desired. In a further embodiment, the intensity of the fluorescent signal is measured at a plurality of locations along the length of microchannel (103). The plurality of locations at which the intensity of the fluorescent signal is measured may be different sections of the microchannel. The plurality of locations at which the intensity of the fluorescent signal is measured may be the entire defined section (i.e., reaction zone) of the microchannel. In a further embodiment, the image capture is performed repeatedly at specific time intervals. The image may be created or the intensity of the fluorescent signal measured using a multiple-pixel array detector (such as a CCD or CMOS image sensor) or a single pixel detector.

Figure 2:
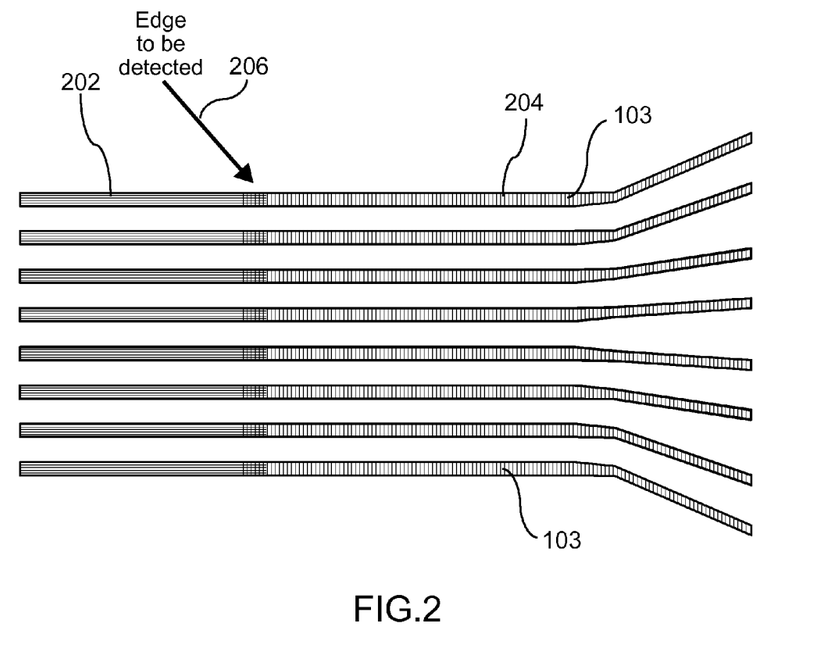
FIG. 2 shows an image of fluid slugs with a fluid transition edge in microchannels of the micro fluidic system as shown in FIG. 1.

FIG. 2 shows an image of microchannels (103) of a micro fluidic device acquired by detector (115) as shown in FIG. 1. Each microchannel (103) includes a sample slug (202) and a blanking slug (204). The sample slug (horizontal hatch region) (202) and the blanking slug (vertical hatch region) (204) have an edge (206) that has to be detected. The detection problem is simplified and takes advantage of the fact that there is only a single edge to be detected in each channel. A biological reaction is performed in each sample slug (202). In one embodiment, the biological reaction is performed in a stopped flow mode when the slugs (202) and (204) are stopped in the microchannel (103). In yet another embodiment, the biological reaction is performed in a continuous flow mode while the slugs (202) and (204) are moving along the microchannel (103). The sample slug (202) includes a blue fluorescent marker and the blanking slug (204) includes a red fluorescent marker. In one aspect of the invention, the image of microchannels (103) as shown in FIG. 2 is acquired throughout the biological reaction and the edge (206) is held steady or oscillated to ensure consistent heating.

Figure 3:
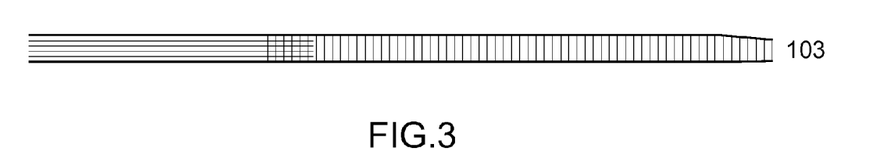
FIG. 3 shows an image of one of the microchannels as shown in FIG. 2.

In one embodiment, the sample slug (202) includes nucleic acids of interest and the biological reaction is a PCR amplification reaction followed by a nucleic acid melting analysis. In one non-limiting embodiment, no more than one sample slug per microchannel (103) is present in a thermal zone of a microfluidic device, and the thermal zone may be used for both PCR amplification and melt data acquisition. That is, a slug need not be moved from one thermal zone in which temperature cycling for a PCR was performed to a different thermal zone for a temperature ramp causing nucleic acid melting. The system having a single sample slug stopped in a microchannel to undergo a biological reaction is described in greater detail in US Patent Application No. 2014/0272927 which is incorporated herein by reference. FIG. 3 shows a close-up on channel fluids from microchannel (103) as demonstrated in FIG. 2.

Figure 4:
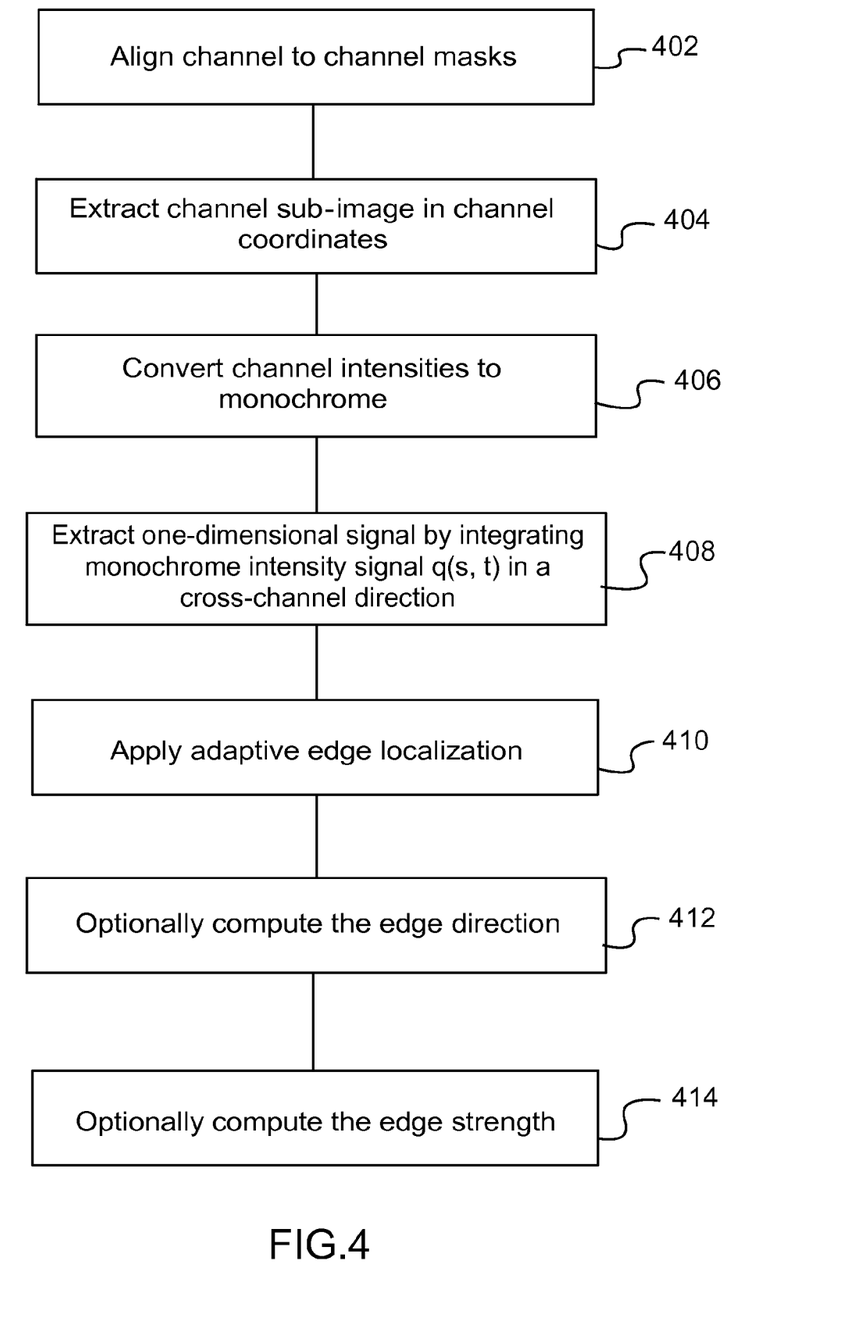
FIG. 4 is a flow chart illustrating a process for detecting position of the edge between adjacent slugs in a microchannel of the microfluidic system according to one embodiment of the present invention.

FIG. 4 is a flow chart illustrating a method for detecting the edge between two adjacent slugs in a microchannel of a microfluidic device according to one embodiment of the present invention. Specifically, in step 402, the image including a plurality of microchannels (103) as shown in FIG. 2 is aligned to mask images for one or more microchannels of interest. In step 404, a channel sub-image characterized by intensity $I(s, t)$ is extracted for each microchannel of interest. In one embodiment, coordinates t and s define the position of each point within the microchannel. Specifically, coordinate t changes along the length of the microchannel from 0 to L, where L is the length of the microchannel. Coordinate s is perpendicular to coordinate t and changes from 0 to W, where W is the width of the microchannel. Accordingly, $I(s, t)$ represents the image intensity having one or more color components at each position within the microchannel defined by coordinate$(s, t)$. In one embodiment, the color components include red, green, and blue such that intensity $I(s, t)$ can be represented as $$I(s, t) = \begin{bmatrix} I(s, t)\text{red} \\ I(s, t)\text{green} \\ I(s, t)\text{blue} \end{bmatrix}.$$

In step 406, the microchannel sub-image represented by intensify $I(s, t)$ is optionally converted to a monochrome image by using transformation P=[Pred, Pgreen, Pblue], where Pred, Pgreen, and Pblue are weights defining contribution of red, green, and blue intensity components to a transformed monochrome signal $q(s, t)=P\ I(s, t)$.

In one embodiment, a single color component, for example red, can be used for the monochrome image. In this case, the transformation P=[1, 0, 0] and $q(s, t)=I(s, t)\text{red}$. In yet another embodiment, different linear and non-linear conversion methods may be used to convert a multi-color image to a monochrome image. Specifically, a conversion can be implemented by using the difference between red and blue color components. In this case, P=[1, 0, −1] and q(s, t)=I(s, t)red−I(s, t)blue. A linear conversion can be described by equation (1) as follows:

$$q(s, t) = PI(s, t) = [Pred, Pgreen, Pblue] \begin{bmatrix} I(s, t)\text{red} \\ I(s, t)\text{green} \\ I(s, t)\text{blue} \end{bmatrix} = \qquad (1)$$

$$PredI(t, s)\text{red} + PgreenI(t, s)\text{green} + PblueI(t, s)\text{blue}$$

In this equation, I(s, t) is the intensity corresponding to the channel sub-image, P is a monochrome image producing transformation having constant elements Pred, Pgreen, Pblue. Transformation P converts intensity I(s, t) having one or more color components to a single value defined by equation (1) for given s and t. In a non-linear conversion in this example, P is a non-linear function of I(s, t)red, I(s, t)green, and I(s, t)blue.

In step 408, a one-dimensional image y(t) is created from the two-dimensional monochrome image represented by intensity q(s, t). Specifically, the monochrome image intensity q(s, t)=PI(s, t) is summed along the cross-channel direction s to provide a one dimensional signal y(t), where y(t) is defined by equation (2):

$$y(t) = \int_0^W PI(s, t) ds, \qquad (2)$$

where W is the channel width.

Equation (2) can also be expressed in discrete form by equation (3), $$y(t) = \Sigma_{s=1}^W PI(s,t), \qquad (3)$$

where s and t are pixel coordinates in the channel region. In this embodiment, the signal is the sum of intensities for each pixel in the cross-channel direction s. Referring to FIG. 2, the intensity associated with the channel (103) comprising sample and blanking slugs (202) and (204) is represented by the one-dimensional intensity signal y(t) defined by equations (2) or (3).

In some embodiments, multiple signals can be produced. For example, one signal for each s value may be produced and processed separately;

$$y_s(t) = q(s,t) \qquad (4)$$

Next, in step 410, the location t* of the edge (206) for two adjacent slugs (202) and (204) as shown in FIG. 2 is determined. In one non-limiting embodiment, to determine the location of the edge (206), a plurality of different segmentations is sequentially applied along the length of the channel thereby partitioning the channel into two regions. Specifically, the first region is defined by the interval [0; t] and the second region is defined by the interval (t; L], where coordinate t takes a specific value from the interval (0; L) for each segmentation.

In yet another non-limiting embodiment, when the image is defined for discrete units, such as the pixels of a digital image, the length of the channel can be said to have L units or pixels and two regions are defined by the sets {1, . . . , t} and {t+1, . . . , L}. Accordingly, t sequentially takes values 1, 2, . . . , L−1 going from the first segmentation to the last segmentation. The number of segmentations applied to the length of the channel that can create two segments equals one less than the number of pixels along the length of the channel.

For each segmentation applied along the length of the microfluidic channel (103), the between class variance, $\sigma^2$ can be calculated for intensity signals $y_1(t)$ and $y_2(t)$ associated with the first and second regions, respectively, i.e. [0; t] and (t; L], by using the following equation:

$$\sigma^2 = \omega_1 \omega_2 [\mu_1 - \mu_2]^2, \qquad (4')$$

where $\omega_1$ is the class probability for the region [0; t], $\omega_2$ is the class probability for the region (t; L], $\mu_1$ is the mean for the intensity signal y(t) in the region [0; t], and $\mu_2$ is the mean for the intensity signal y(t) in the region (t; L]. For each segmentation as described above, we have intensity signal $$y(t), \omega_1 = \frac{t}{L}, \omega_2 = \frac{L-t}{L}, \mu_1 = \frac{\int_0^t y(\tau) d\tau}{t}, \text{ and } \mu_2 = \frac{\int_t^L y(\tau) d\tau}{L-t}.$$

Based upon the equations above, the between class variance can be calculated as $$\sigma^2 = \frac{z^2(L)}{L^2} \frac{\left[\frac{z(t)}{z(L)} \frac{t}{L}\right]^2}{\frac{t}{L}\left(1 - \frac{t}{L}\right)}, \text{ where } z(t) = \int_0^t y(\tau) d\tau$$

Based on Otsu's method that requires maximization of the between class variance, the edge location t* maximizes the following equation:

$$\max_t \frac{\left[\frac{z(t)}{z(L)} \frac{t}{L}\right]^2}{\frac{t}{L}\left(1 - \frac{t}{L}\right)} = \max_t v(t), \qquad (5)$$

wherein v(t) is called edge score function, t ranges from 0 to L (the length of the channel sub-image), or from 1 to L−1 in the discrete image case, and z(t) is the cumulative sum of the signal y(t).

$$z(t) = \int_0^t y(\tau) d\tau \qquad (6)$$

In one non-limiting embodiment, z(t) can be presented in a discrete form as $$z(t) = z(t-1) + y(t)$$

$$z(0) = 0 \qquad (7)$$

As $$\frac{z^2(L)}{L^2}$$

is a finite positive number independent of t, the coefficient $$\frac{z^2(L)}{L^2}$$

will not affect t* resulting from equation (5).

In step 412, after determining the location of the edge (206) by finding t* that maximizes the edge score function v(t), the edge direction is optionally calculated by calculating the left and right mean signal values according to equations $$\mu_{LEFT} = \frac{z(t^*)}{t^*} \text{ and } \mu_{RIGHT} = \frac{z(L) - z(t^*)}{L - t^*}.$$

If $\mu_{LEFT}$ is larger than $\mu_{RIGHT}$ then the edge is transitioning from high to low intensity as the channel image is scanned from the left to the right. Otherwise the edge is transitioning from low to high intensity. Next, in one non-limiting embodiment, the difference between $\mu_{LEFT}$ and $\mu_{RIGHT}$ is used as a means to score the strength of the edge in step 414.

As noted above, the location of the edge (206) between two adjacent slugs (202) and (204), t*, is determined in step 410. The process for calculating t* maximizing the edge score function v(t) as reflected in step 410 of FIG. 4 is presented in greater detail in a flow chart shown in FIG. 5.

Figure 5:
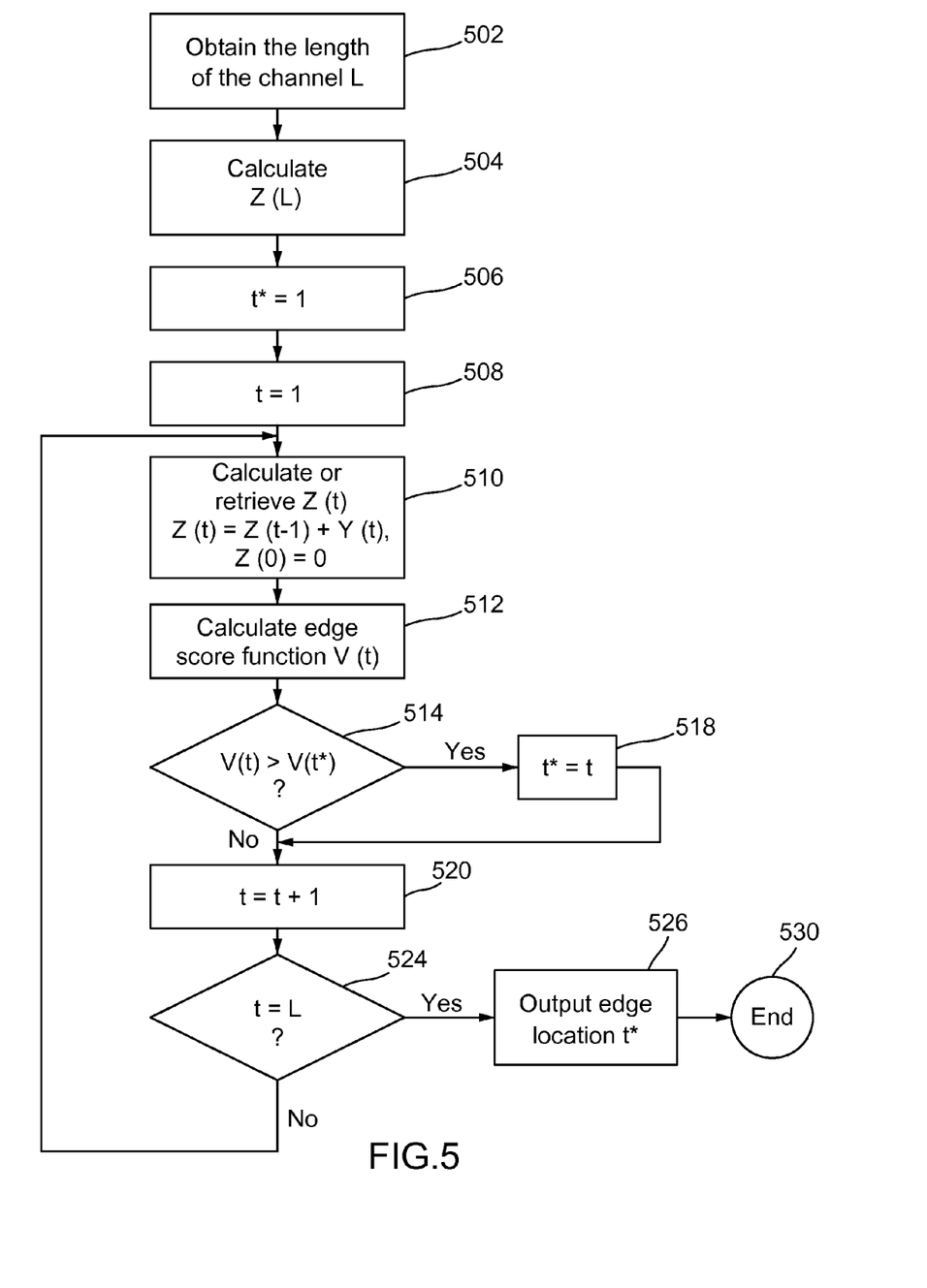
FIG. 5 is a flow chart illustrating a process for determining the location of the edge between adjacent slugs in a microchannel based upon an edge score function according to one embodiment of the present invention.

Specifically, in step 502, the length of a microchannel, L, is obtained. Next, the signal sum, z(L), is calculated according to equation (7) in step 504. In step 506, the location of the edge, t*, is set to 1. In step 508, the location t selected along the microchannel is set to 1. In step 510, the signal cumulative sum z(t)=z(t−1)+y(t), where z(0)=0, is calculated. Alternatively, the results of z(t) for each value of t may be retrieved if it was saved in the calculation of S in step 504. Next, in step 512, the edge score function v(t), that is the objective of the maximization in equation (5), is calculated for t given z(t) from step 510, z(L) from, step 504, and L from step 502. In step 514, a determination is made whether v(t) is greater than v(t*). If the result of the determination is positive (v(t)>v(t*)), t* is set to be equal to t (step 518) and flow continues to step 520. If the result of the determination made in step 514 is negative (v(t)<v(t*)) the process proceeds directly to step 520. In step 520 t is set to be equal to t+1. Next, if it is determined that t=L in step 524, t* is output as the location of the edge between two adjacent slugs in the microchannel (step 526) and the process ends at step 530.

If it is determined in step 524 that the condition t=L is false, the process goes back to step 510. Accordingly, the method described in FIGS. 4 and 5 uses thresholding in a coordinate domain t and as such the edge location t* represents an optimal threshold. It should be clear to one skilled in the art that several permutations of this process are possible by performing these tasks in various orders or by modifying the flow of the process and that this example should be considered a non-limiting embodiment.

In one embodiment corresponding to equation (4), where multiple signals are to be analyzed, the edge location may be estimated from the plurality of channel signals by using the mean or median of the detected locations for example.

The above formulation given by equation (5) is based on Otsu's method for adaptive thresholding used in the related art to generate the high intensity blobs from which the edge is derived. Otsu's method is based on the idea that the intensity signal corresponding to the edge location should maximize the between class variance for intensities corresponding to the blobs and uses thresholding in the intensity domain. In contrast, the method according to the present invention uses thresholding in the coordinate domain as the derivations above are provided for a single slug edge that breaks the channel into two regions. Unlike the related art, the method of the present invention is insensitive to high levels of noise associated with intensity signal measurements. Also, the method is extremely computationally efficient requiring computation on the order of O(W·L).

Figure 6A:
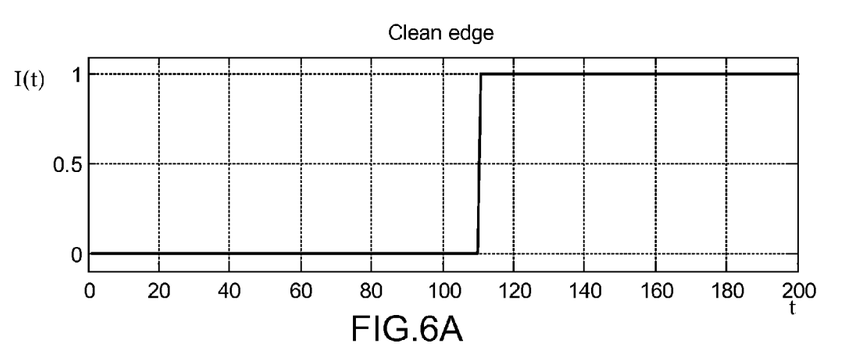
FIG. 6A shows a clean edge monochrome intensity signal changing along the length of a channel.
Figure 6B:
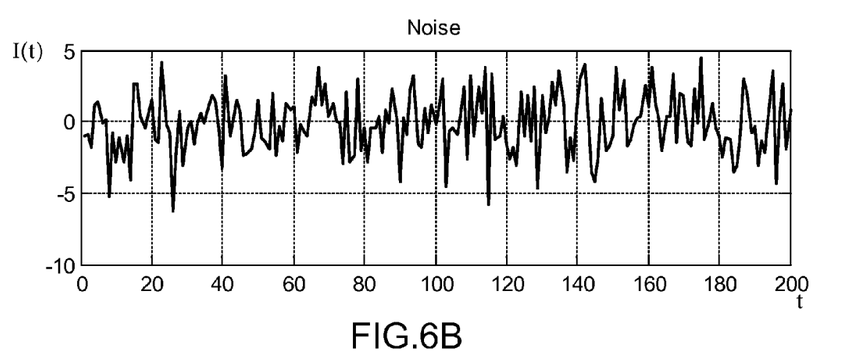
FIG. 6B shows white Gaussian noise in a channel image.
Figure 6C:
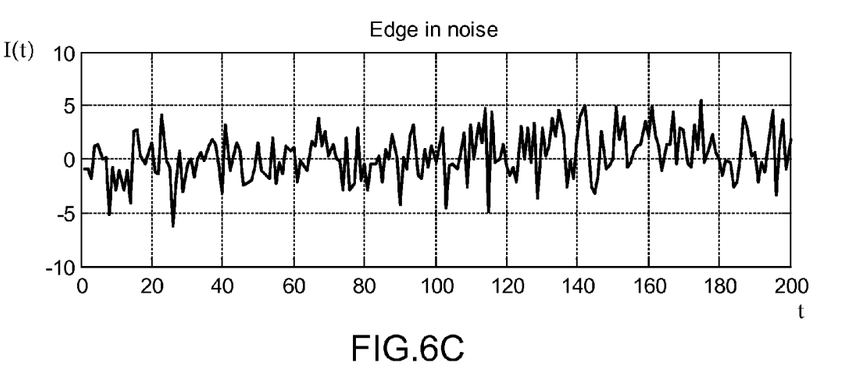
FIG. 6C shows white Gaussian noise of FIG. 6B and the clean edge intensity signal of FIG. 6A added together to simulate a noisy intensity signal changing along the length of the channel.
Figure 7A:
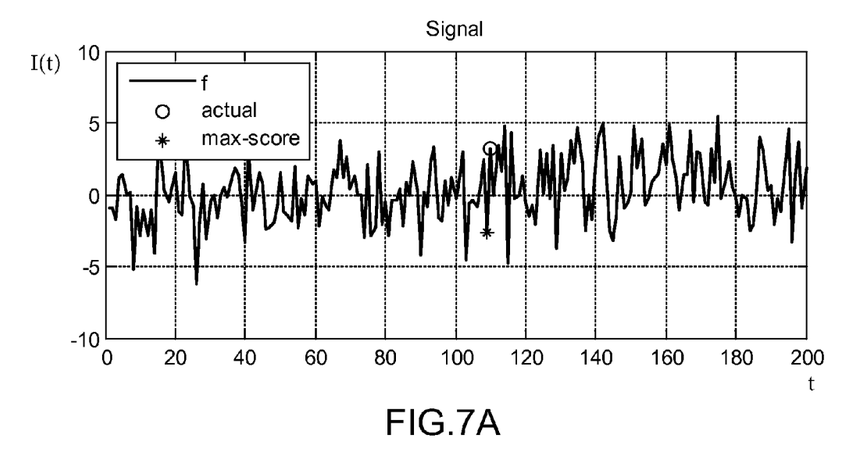
FIG. 7A shows a noisy monochrome intensify signal generated according to FIG. 6C.
Figure 7B:
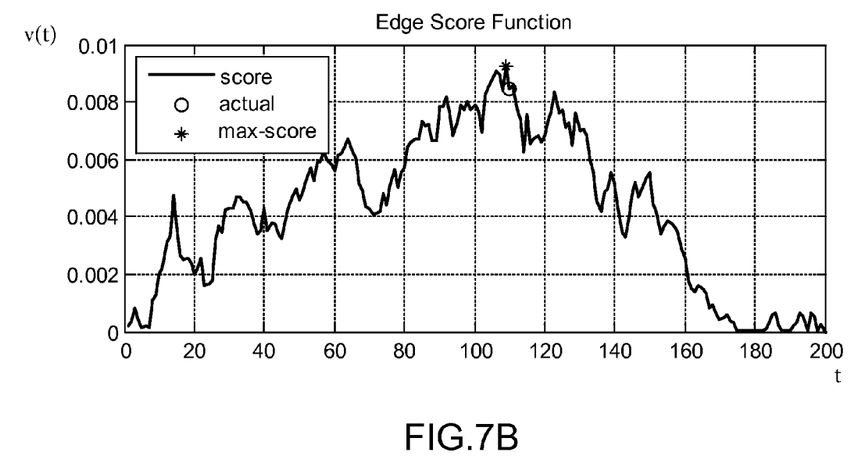
FIG. 7B shows an edge score as a function changing along the length of the channel.

FIGS. 6 and 7 show an example of the technique as described in FIGS. 4 and 5 that is applied to an image characterized by an intensity signal acquired along the length of a microchannel having two adjacent slugs of different colors. FIG. 6B shows simulated noise corresponding to intensity I(t) changing along the length of the microchannel. The original edge location is shown in FIG. 6A. Specifically, a step from zero to one is depicted at a randomly selected location corresponding to the edge between two adjacent slugs in the microchannel. As shown in FIG. 6B, the noise is Gaussian, independent, and identically distributed along the microchannel, with the mean of zero and a standard deviation of two. FIG. 6C shows the noise from FIG. 6B added to the original edge signal from FIG. 6A. As, the edge shown in FIG. 6C is not very perceptible to the human eye, the method according to the present invention demonstrated in FIG. 5 is applied to determine the edge location. Specifically, FIG. 7B shows edge score function v(t) calculated according to equation (5) and used for determining the edge location along the length of the channel.

FIG. 7A shows an original noisy signal as a function of the position along the length of a microchannel. A detected edge location (702) and an actual edge location (704) are shown with an asterisk and a circle, respectively. The edge location (702) is defected according to the method described in FIG. 5 and is within one pixel of the actual edge location (704) despite the heavy noise. Additionally, FIG. 7B shows the edge score function v(t) changing along the length of the channel according to equation (5). The detected edge location (702) and the actual edge location (704) are shown with an asterisk and a circle, respectively in FIG. 7B. It can be seen from FIG. 7B that coordinate t for the detected edge location (702) and the actual edge location (704) maximize the edge score function v(t) calculated according to equation (5).

In yet another embodiment, the method according to the present invention as shown in FIG. 4 and FIG. 5 can be extended to a channel having multiple slugs if the number of slugs is known or presumed to be known. If multiple slugs are expected, the method can search over the space of the multiple thresholds. For example for two edges, the algorithm can search over $t^*_1$ and $t^*_2$, where $t^*_1 < t^*_2$. This approach is of computational complexity of $O(L^n)$, where n is the number of thresholds to be found. Alternatively, a faster approach might be to search for the thresholds recursively where the above algorithm is first applied to find a first threshold. Then the left and right partitions are scanned with the above algorithm to find a second and third threshold. The strength of the edges can be used to determine whether the edge is significant or not. Thus in this approach, the method may automatically make a determination of the number of edges. This recursive approach is of computational complexity O(L log L).

In yet another non-limiting embodiment, the method can be adapted to changes in intensity in the channel direction that occur due to illumination conditions or camera setup. This method is faster and less sensitive to noise and other artifacts.

Other embodiments include finding the maximum of a smoothed version of the edge score function described by equation (5).

Figure 8:
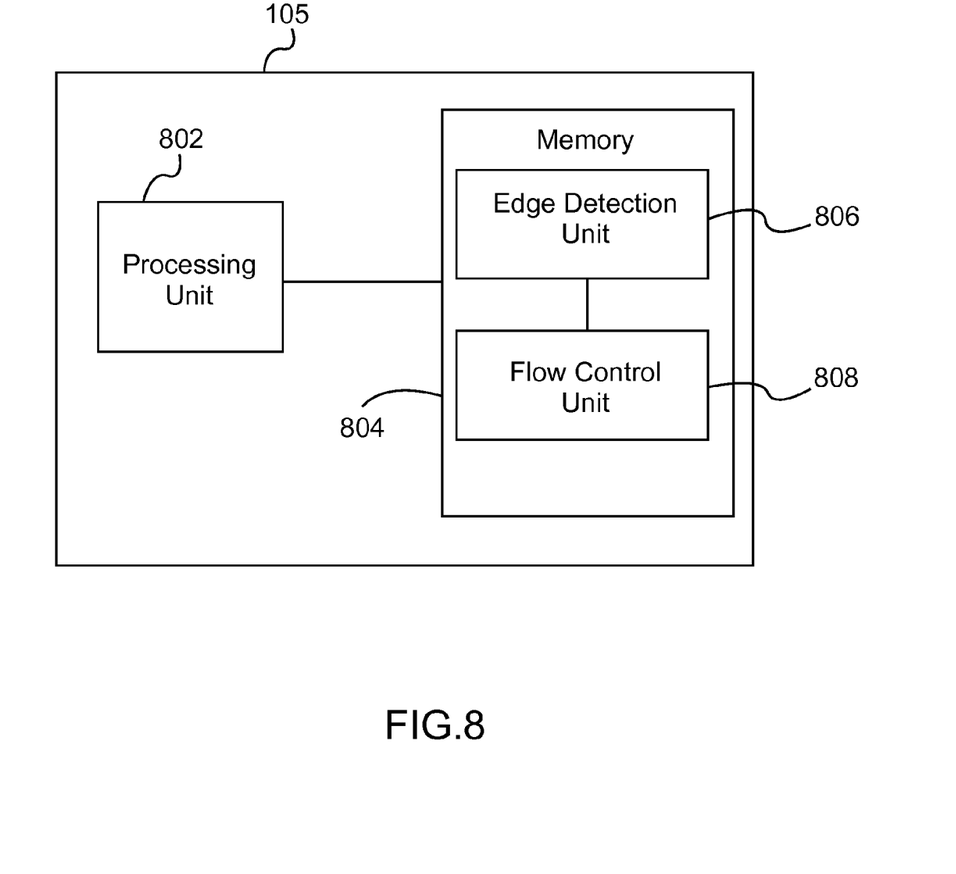
FIG. 8 is a block diagram illustrating a fluid control system according to the present invention.

FIG. 8 is a block diagram illustrating a control system according to the present invention. The main control and processing computer (105) shown in FIG. 1 includes a processing unit (802) in communication with memory (804). Memory (804) includes an edge detection unit (806) in communication with a flow control unit (808). The edge detection unit comprises instructions executed by the processing unit (802) to determine the edge position along the length of microchannel (103) according to the method presented in FIG. 4. Once the position of the edge (206) is determined, the flow control unit provides instructions to evaluate the positions of the slugs (202) and (204) in microchannel (103) and controls the fluid flow in microchannel (103) by providing instructions to pump mechanism (106) in order to regulate the flow of the test solution and the carrier fluid in microchannel (103) by positive pressure at the upstream side or inlet of microchannel (103) or by negative pressure at the downstream side or outlet of microchannel (103).

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

The invention claimed is:

1. A system comprising:
a channel having two adjacent fluid slugs positioned along the channel, the slugs having a color gradient across an edge;
an image sensor configured to acquire an image of at least a portion of the adjacent fluid slugs in the channel, the acquired image characterized by an intensity signal changing at least along the channel;
non-transitory media in communication with a processing unit, the non-transitory media comprising an edge detection unit in communication with the image sensor, the edge detection unit providing instructions to the processing unit to:
sequentially apply at least two different segmentations to the length of the channel, each segmentation partitioning the length of the channel into two segments, left segment and right segment, at a specific location;
for each of the at least two segmentations, calculate an edge score function proportional to a between class variance for intensity signal values associated with the two adjacent segments, wherein the between class variance is calculated based upon a probability for each of the two adjacent segments and a mean value of the intensity signal in each of the two adjacent segments; and
select a segmentation defining an edge between the two adjacent fluid slugs based at least in part on the edge score function, wherein a location of the edge between the two adjacent slugs is defined as a coordinate of the specific location selected along the length of the channel to separate the two adjacent segments in the selected segmentation.

2. The system of claim 1, wherein the segmentations are sequentially applied to the length of the channel such that a coordinate of the specific location defining a segmentation is uniformly increasing from a first segmentation to a last segmentation.

3. A system of claim 1, where the intensity signal is an one-dimensional signal changing along the length of the channel.

4. A system of claim 1, wherein the intensity signal is a two-dimensional signal changing along and across the channel, the two-dimensional intensity signal being converted into an one-dimensional intensity signal by integrating the two-dimensional intensity signal in a cross channel direction.

5. The system of claim 1, wherein the segmentation defining the location of the edge between adjacent slugs is selected to maximize the edge score function.

6. The system of claim 1, wherein the detection unit further comprises instructions for converting the intensity signal having one or more color components at each position in the channel to a monochrome signal having a single color component.

7. The system of claim 6, wherein the between class variance is calculated as $$\sigma^2(t) = K \frac{\left[\frac{z(t)}{z(L)} - \frac{t}{L}\right]^2}{\frac{t}{L}\left(1 - \frac{t}{L}\right)} = K v(t),$$

where L is the length of the channel, t is coordinate changing along the length of channel, W is the width of the channel, $z(t)=\int_0^t y(\tau)d\tau$, $y(t)=\int_0^W P\ I(s, t)ds$, $v(t)$ is the edge score function, s is a coordinate orthogonal to t, $I(s, t)$ is an intensity, P is a monochrome image producing transformation, and K is any finite positive number that is independent of t.

8. The system of claim 1, wherein the number of sequential segmentations applied to the length of the channel equals the number of pixels along the length of the channel.

9. The system of claim 4, wherein the acquired image of the channel having two adjacent fluid slugs is aligned to a channel mask prior to integrating the two-dimensional intensity signal in a cross channel direction.

10. The system of claim 1, wherein left and right mean intensity signal values corresponding to left and right segments of the channel, respectively, are calculated for the determined edge location and an edge direction is calculated based upon the determined left and right mean signal values, wherein the edge direction distinguishes which side of the edge corresponds to which fluid slug.

11. The system of claim 10, wherein the left and right mean intensity signals are calculated as $$\mu_{LEFT} = \frac{z(t^*)}{t^*} \text{ and } \mu_{RIGHT} = \frac{z(L) - z(t^*)}{L - t^*},$$

where t* defines the edge between the two adjacent slugs.

12. The system of claim 1, further comprising a flow control unit to control fluid flow in the channel based on the determined edge location.

13. The system of claim 1, further comprising a microfluidic chip, wherein the channel is a microchannel formed in the microfluidic chip.

14. The system of claim 13, wherein the microchannel includes one sample slug undergoing a biological reaction and one blanking slug.

15. The system of claim 13, wherein the biological reaction is performed in a stopped or continues flow mode.

16. The system of claim 14, wherein the sample slug includes a first fluorescent color marker and the blanking slug includes a second fluorescent color marker.

17. The system of claim 14, wherein one sample slug includes nucleic acids, wherein the biological reaction performed in the sample slug includes a PCR amplification reaction and nucleic acid melting analysis.

18. A method comprising:
providing a channel having two adjacent fluid slugs positioned along the channel, the slugs having color gradient across an edge;
providing an image detector in communication with an edge detection unit;
acquiring, by an image detector, an image of at least a portion of the two adjacent fluid slugs in the channel, the acquired image characterized by an intensity signal changing at least along the channel;
sequentially applying at least two different segmentations to the length of the channel, each segmentation partitioning the length of the channel into two adjacent segments, left segment and right segment, at a specific location selected along the length of the channel;
for each segmentation, calculating a between class variance for intensity values associated with the two adjacent segments, wherein the between class variance is calculated based upon a class probability for each of the two adjacent segments and a mean value of the intensity signal in each of the two adjacent segments; and
selecting a segmentation defining an edge between the two adjacent fluid slugs based at least in part on the between class variance, wherein a location of the edge between the adjacent slugs is defined as a coordinate of the specific location separating the two adjacent segments in the selected segmentation.

19. The method of claim 18, wherein the segmentations are sequentially applied to the length of the channel such that a coordinate of the specific location defining a segmentation is uniformly increasing from a first segmentation to a last segmentation.

20. A method of claim 18, where the intensity signal is a one-dimensional signal changing along the length of the channel.

21. A method of claim 18, wherein the intensity signal is a two-dimensional signal changing along and across the channel, the two-dimensional intensity signal being converted into an one-dimensional intensity signal by integrating the two-dimensional intensity signal in a cross channel direction.

22. The method of claim 18, wherein the segmentation defining the location of the edge between adjacent slugs is selected to maximize the between class variance.

23. The method of claim 18, further comprising converting the intensity signal having one or more color components at each position in the channel to a monochrome signal having a single color component.

24. The method of claim 21, wherein the between class variance is calculated as $$\sigma^2(t) = K \frac{\left[\frac{z(t)}{z(L)} \frac{t}{L}\right]^2}{\frac{t}{L}\left(1 - \frac{t}{L}\right)},$$

where L is the length of the channel, t is a coordinate changing along the length of the channel, W is the width of the channel, $z(t) = \int_0^t y(\tau)d\tau$, $y(t) = \int_0^W P\, I(s, t)ds$, s is a coordinate orthogonal to t, I(s, t) is an intensity, P is a monochrome image producing transformation, and K is any finite positive number that is independent of t.

25. The method of claim 18, wherein the number of sequential segmentations applied to the length of the channel equals the number of pixels along the length of the channel.

26. The method of claim 18, wherein the fluid slugs are stopped in the channel.

27. The method of claim 21, wherein the image of the channel having two adjacent fluid slugs is aligned to a channel masks prior to integrating the two-dimensional intensity signal in a cross channel direction.

28. The method of claim 18, wherein left and right mean intensity signal values corresponding to left and right segments of the channel, respectively, are calculated for the determined edge location and an edge direction is calculated based upon the determined left and right mean signal values.

29. The method of claim 28, wherein the left and right mean intensity signals are calculated as $$\mu_{LEFT} = \frac{z(t^*)}{t^*} \text{ and } \mu_{RIGHT} = \frac{z(L) - z(t^*)}{L - t^*},$$

where t* defines the edge between the two adjacent slugs.

30. The method of claim 18, further comprising controlling fluid flow in the channel based on the determined edge location.

31. The method of claim 18, wherein the channel is a microchannel formed in a microfluidic chip.

32. The method of claim 31, wherein the microchannel includes one sample slug undergoing a biological reaction and one blanking slug.

33. The system of claim 32, wherein the biological reaction is performed in the sample slug in a stopped or continues flow mode.

34. The system of claim 32, wherein the sample slug includes a first fluorescent color marker and the blanking slug includes a second fluorescent color marker.

35. The method of claim 32, wherein the at least one sample slug includes nucleic acids, wherein the biological reaction performed in the sample slug includes a PCR amplification reaction and nucleic acid melting analysis.

* * * * *